United States Patent [19]

Costagliola

[11] Patent Number: 4,813,414

[45] Date of Patent: Mar. 21, 1989

[54] DEVICE FOR GARROTING THE BREAST

[75] Inventor: Michel Costagliola, Toulouse, France

[73] Assignee: Walton Medical, Saint Denis, France

[21] Appl. No.: 923,156

[22] PCT Filed: Feb. 5, 1986

[86] PCT No.: PCT/FR86/00032

§ 371 Date: Oct. 8, 1986

§ 102(e) Date: Oct. 8, 1986

[87] PCT Pub. No.: WO86/04804

PCT Pub. Date: Aug. 28, 1986

[30] Foreign Application Priority Data

Feb. 21, 1985 [FR] France .................... 85 02517

[51] Int. Cl.⁴ .............................................. A61B 17/00
[52] U.S. Cl. .................... 128/303 R; 128/346; 81/3.44
[58] Field of Search ............ 128/303 R, 320, 321, 128/323, 325, 346, 20; 81/3.44, 3.4, 330

[56] References Cited

U.S. PATENT DOCUMENTS

| | | | |
|---|---|---|---|
| 183,602 | 10/1876 | Strubell | 128/346 |
| 1,947,649 | 2/1934 | Kadavy | 128/303 R |
| 1,983,969 | 12/1934 | Davis | 128/346 |
| 2,100,730 | 11/1937 | Black | 128/346 |
| 2,523,544 | 9/1950 | Stamp | 81/3.44 |
| 4,205,681 | 6/1980 | Nestor et al. | 128/321 |
| 4,249,534 | 2/1981 | Muldrow, Jr. | 128/319 |
| 4,662,356 | 5/1987 | Aronsohn | 128/346 |

Primary Examiner—Dalton L. Truluck
Assistant Examiner—Denise Whelton
Attorney, Agent, or Firm—Marvin Feldman

[57] ABSTRACT

A device is formed with two hinged half-collars for opening and closing around the breast, which half-collars have specifically contoured inside surfaces which surfaces correlate to orthogonally projected curves which intersect at an angle slightly less than 180° but not less than about 160° over the useful clamping of the half-collars, to effectively clamp the breast while avoiding pinching during clamping of the half-collars on the breast.

4 Claims, 2 Drawing Sheets

DEVICE FOR GARROTING THE BREAST

TECHNICAL FIELD

The invention relates to a device for garroting the breast for use, in particular in plastic surgery operations.

PRIOR ART

Surgery for mammary hypertrophy has become a routine operation for most plastic surgeons.

A common feature of modern techniques is the conservation of a de-epidermized thermo-glandular plate around the areola in order to provide good vascularization of the areolo-mammilary plate of the remaining glandular tissue.

The technique of de-epidermization requires the skin to be put under tension by garroting the root of the gland. Most surgeons use a knotted strip of cloth or else they need an operating theatre assistant to perform the garroting by hand.

The aim of the invention is to provide powerful and stable garroting putting the skin under maximum tension, thereby facilitating the act of de-epidermization which then becomes more accurate, and above all more rapid.

SUMMARY OF THE INVENTION

The invention provides a device for garroting the breast, characterized in that it comprises a collar of rigid material having an adjustable opening suitable for surrounding the breast and for coming into engagement therewith, and lockable in the adjusted position.

BRIEF DESCRIPTION OF THE DRRAWINGS

Other characteristics and advantages of the invention appear from the following detailed description and the accompanying drawings, in which.

BEST METHOD OF PERFORMING THE INVENTION

Figure 1:
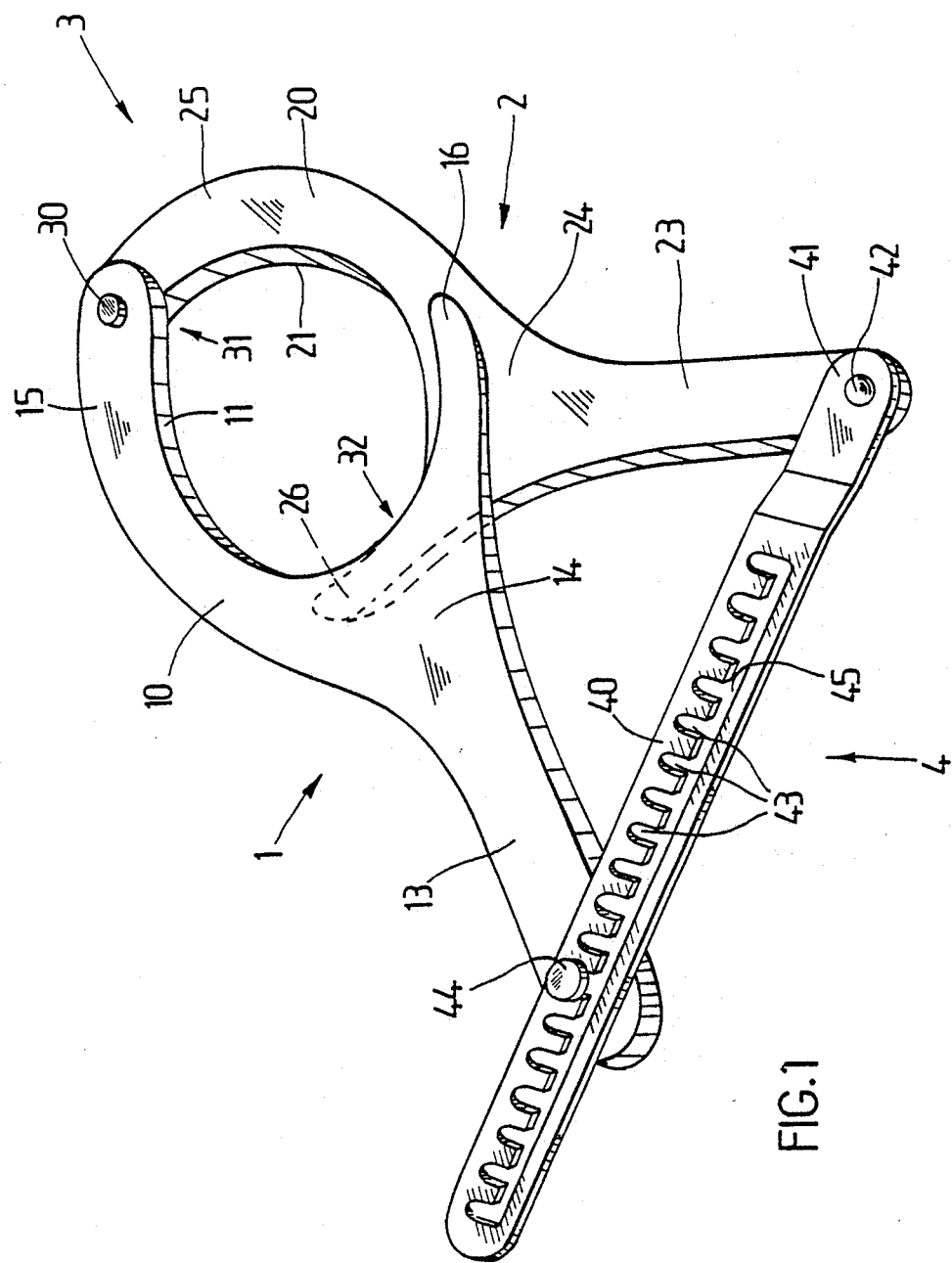
FIG. 1 is a perspective view of a device in accordance with the invention.

The device shown in FIG. 1 essentially comprises two one-piece parts 1 and 2 capable of rotating relative to each other about a pin 30, together with a ratchet-shaped bar cooperating with the parts 1 and 2 in order to hold them stably in different relative positions.

The parts 1 and 2 are identical in shape with items on the part 1 being designated in the drawings by reference numerals obtained by adding the number 10 to the reference numerals of the corresponding items on the part 1.

The part 1 is delimited by two plane faces perpendicular to the pin 30 and comprises a handle or branch 13, an arcuate portion 15 extending from one end 14 of the handle 13 to the pin 30 which passes through the portion 15, and a horn-shaped portion 16 extending from the end 14 towards the end 24 of the handle 23 of the part 2. The arcuate and horn-shaped portions 15 and 16 together constitute a rigid jaw or half-collar 10 having an inside surface 11 which is situated substantially opposite the corresponding surface 21 of the jaw 20. Together the surfaces 11 and 21 constitute the inside contour of a deformable ring or collar 30 capable of being clamped around the breast to be treated by relative movement of the parts 1 and 3. The surfaces 11 and 21 run into each other in a first zone 31 close to the pin 30 and in a second zone 32 further away from said pin. The zones 31 and 32 whose positions along the surfaces 11 and 21 vary as a function of the relative positions of the parts 1 and 2 delimit between each other portions of the surfaces 11 and 21 which constitute the inside contour of the ring, which is substantially oval in shape and which is intended to come into direct contact with the breast. In the configuration shown in FIG. 1, the surfaces 11 and 21 extend beyond the zone 32, outwardly of said contour.

An elongate link member or ratchet 40 has one end 41 attached to a hinge member fixed relative to the jaw 20 and constituted by a pin 42 mounted on the handle 23 close to its free end, and has a plurality of transverse slots 43 distributed along its length and each capable of being selected to loosely receive a peg 46 which is fixed to the jaw 10 and carried on the free end of the handle 13.

Figure 2:
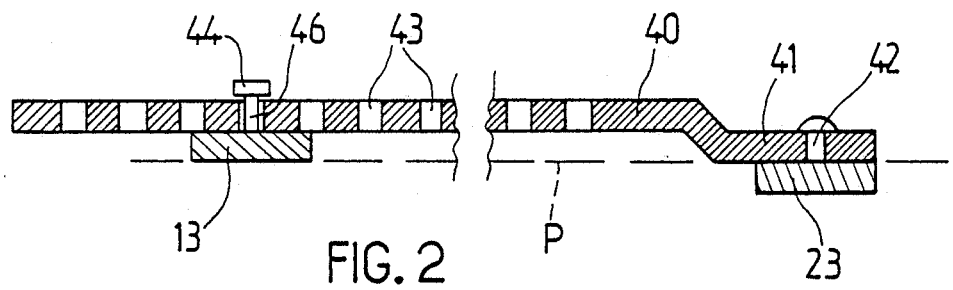
FIG. 2 is a fragmentary section view through the FIG. 1 device.

The section of FIG. 2 is taken on a plane passing through the pin 42 and the axis of the peg 46, and passing through the slot 43. As can be seen in FIG. 1, each of the slots 43 is closed at one end and communicates via its opposite end with a longitudinal slot 45 in which the peg 46 is capable of moving freely. The slots are inclined relative to the longitudinal direction of the ratchet so that their closed ends are further from the pin 42 than their opposite ends. The peg 46 is terminated by a head 44 which is larger in size than the with of the slots.

The parts 1 and 2 are situated on either side of a plane P (see FIG. 2) perpendicular to the pin 30 and in which one of the plane faces of each of said parts extends substantially. The parts therefore do not impede mutual movement.

The device is used in the following manner. Firstly the ring 3 is opened by moving the lever-forming extensions 13 and 23 away from each other, with the peg 46 running along the slot 45 towards the free end of the ratchet, until the inside perimeter of the ring is substantially larger than the perimeter of the breast to be garroted.

The jaws are then passed around the breast and brought towards each other by acting on their extensions 13 and 23 in order to clamp the ring 3 around the breast. The peg 44 then moves along the slot 45 towards the end 41 of the ratchet. Once the desired skin tension has been achieved, the peg 46 is engaged in the nearest slot 43 by slightly pivoting the ratchet about the pin 42. The reaction of the breast against the jaws tends to separate the jaws and moves the peg 46 to the closed end of the inclined slot 43 and brings it into abutment therewith. The jaws are now fixed relative to each other and keep the skin under tension.

In order to unlock the device, the handles are moved a small distance towards each other and the ratchet is pivoted in opposite direction to return the peg 46 into the slot 45, thereby allowing the parts 1 and 2 to be moved apart again, thus releasing the breast.

Figure 3:
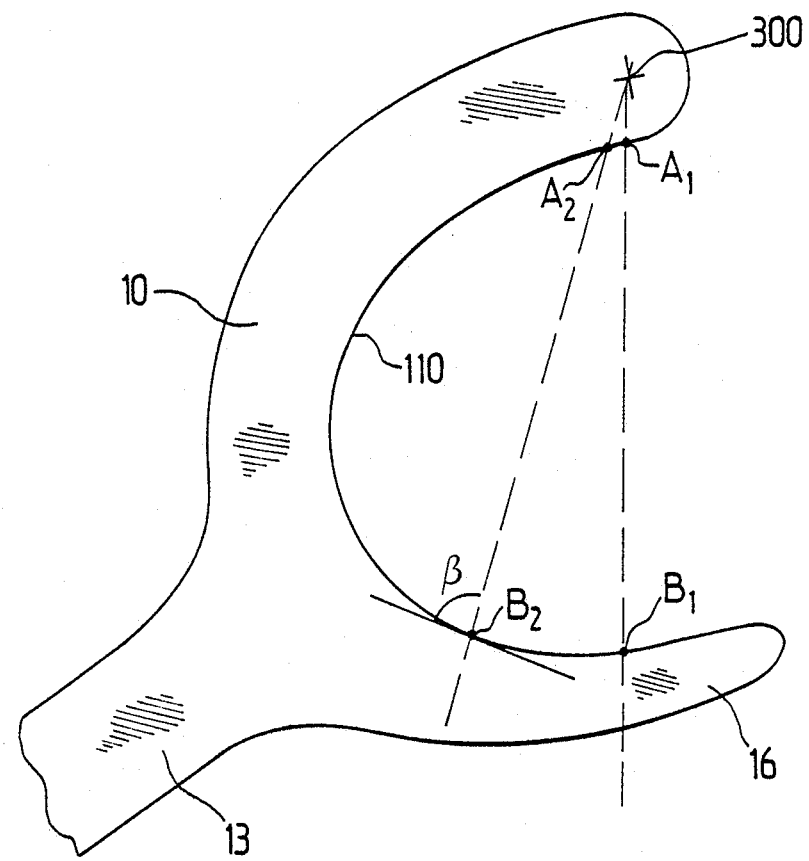
FIG. 3 is a profile of one jaw of the device.

FIG. 3 shows the profile of one of the jaws, designated by the reference 10, and as it appears in an orthogonal projection onto a plane perpendicular to the pin 30, and it is recalled that the shape of the jaw 20 is similar to that of the jaw 10.

The inside surface 11 of the jaw is represented by a curve 110 which approximately constitutes the projection thereof, since the surface is substantially that of a cylinder traced by a generator line parallel to the pin 30.

The device is designed to have a useful stroke over which the junction zone 31 between the surfaces 11 and 21 moves along the surface 11 between a position represented by a point A1 and a position represented by a point A2 on the curve 110, while the zone 2 moves between positions represented by points B1 and B2 on the curve 110. The curve 110 and the corresponding curve for the jaw 20 (not shown) are symmetrical to each other in each position about the corresponding line AB, with the lines AB passing through the axis 300 of the pin 30. The useful stroke defined in this way corresponds to the process of clamping the breast, with the points A and B representing the zones 31 and 32 travelling at most over the arcs A1–A2 and B1–B2 respectively between the moment when the jaws engage the breast and the moment when the desired clamping has been achieved.

The acute angle $\beta$ between the curve 110 and the axis of symmetry which is shown in the figure for its position A2–B2, is slightly less than a right angle and is preferably greater than or equal to about 80° over the useful stroke of the device. The angle $\alpha$ between the curve 110 and the corrsponding similar curve of the jaw 20 is then greater than or equal to about 160°, thereby avoiding pinching the skin during clamping. The angle $\alpha$ may be flat over a portion of the stroke. The angle formed by the curves in the zone 31 must not be too sharp either, but its value is less critical because of the small linear displacement in this zone and the lesser pressure exerted on the breast at this point.

The shape of the arc of the curve A1, A2, B2, B1 shown in FIG. 3 which has its concave side facing the analogous arc of the jaw 20 has been determined experimentally so as to obtain uniform tension of the skin when the device is used with a useful stroke represented by the arcs A1–A2 and B1–B2. This shape thus constitutes a preferred characteristic of the invention.

In order to benefit from the advantages of this particular shape with breasts of all sizes, i.e. without having recourse to a useful stroke greater than that defined above, devices of different sizes must be used depending on the breast size, with the curves 110 then being geometrically similar in shape. Three sizes appear to suffice for treating all the cases which arise.

Modifications may be made to the embodiments described and shown above without going beyond the scope of the invention.

For example, the longitudinal slot 45 of the ratchet may be omitted, with the notches 43 then opening out into to a long side of the ratchet. This disposition makes it possible to fold the instrument to occupy a small space when not in use.

I claim:

1. A device for garroting the breast comprising, a collar of rigid matrial (3) comprising two half-collars (10,20) and a hinge (30) for adjustably opening and closing the collar for surrounding and engaging the breast, said half-collar including surfaces (11,21) forming an inside contour, said surfaces being oppositely disposed, and said inside contour being substantially oval in shape, characterized in that said surfaces are adjacent to each other in a first zone (31) close to the hinge (30) of the collar and in a second zone (32) which is further from said hinge, further characterized in that portions of said surfaces extending between and including said first and second zones orthogonally project onto a plane perpendicular to the hinge (30) axis of the collar at approximately in the form of two respective curves having concave sides, with the concave sides of said curves between said first and second zones facing each other, and further characterized in that said curves cross in the second zone at an angle equal to or slightly less than 180°, and not less than about 160°, over stroke of relative movement between the half-collars corresponding to effective breast clamping while avoiding pinching during closing.

2. A device according to claim 1, characterized in that each of the half-collars (10,20) is provided with an extension (13, 23) and that the collar is locked in the adjusted position by fixing said extensions relative to each other.

3. A device according to claim 2, further comprising a bar (40), characterized in that the extensions include two respective branches between the ends of which said bar (40) is interposed.

4. A device according to claim 3, characterized in that the bar (40) has one of its ends (41) hinged to the end of one of the branches (23) and is fixable to the end of other branch (13) at a multiplicity of points thereof.

* * * * *